(12) United States Patent
Papirov et al.

(10) Patent No.: US 8,202,477 B2
(45) Date of Patent: Jun. 19, 2012

(54) MAGNESIUM-BASED ALLOY

(75) Inventors: Igor Isakovich Papirov, Kharkov (UA); Anatoliy Ivanovitch Pikalov, Kharkov (UA); Vladimir Sergeevitch Shokurov, Kharkov (UA); Sergey Vladimirovitch Sivtsov, Khakov (UA)

(73) Assignee: Acrostak Corp. BVI, Winterthur (CH)

( * ) Notice: Subject to any disclaimer, the term of this patent is extended or adjusted under 35 U.S.C. 154(b) by 146 days.

(21) Appl. No.: 12/599,023

(22) PCT Filed: May 5, 2008

(86) PCT No.: PCT/EP2008/003585
§ 371 (c)(1),
(2), (4) Date: Nov. 5, 2009

(87) PCT Pub. No.: WO2008/145244
PCT Pub. Date: Dec. 4, 2008

(65) Prior Publication Data
US 2010/0161031 A1    Jun. 24, 2010

(30) Foreign Application Priority Data

May 28, 2007 (EP) .................................. 07010557

(51) Int. Cl.
*C22C 23/06* (2006.01)
*A61F 2/06* (2006.01)
(52) U.S. Cl. .................... 420/402; 623/1.38; 606/908
(58) Field of Classification Search .................. 420/402, 420/414, 542–547; 148/420, 406; 623/1.11–1.54
See application file for complete search history.

(56) References Cited

U.S. PATENT DOCUMENTS

| | | | |
|---|---|---|---|
| 5,059,390 A | 10/1991 | Burleigh et al. | |
| 5,238,646 A | 8/1993 | Tarcy et al. | |
| 6,193,817 B1 | 2/2001 | King et al. | |
| 6,395,224 B1 | 5/2002 | Nishino et al. | |
| 6,838,049 B2 | 1/2005 | Fukuzumi et al. | |
| 6,908,516 B2 * | 6/2005 | Hehmann et al. | 420/402 |
| 2002/0159914 A1 * | 10/2002 | Yeh | 420/580 |
| 2003/0129074 A1 | 7/2003 | Bronfin et al. | |
| 2004/0098108 A1 | 5/2004 | Harder et al. | |
| 2004/0241036 A1 | 12/2004 | Meyer-Lindenberg et al. | |
| 2005/0095166 A1 | 5/2005 | Saikawa | |
| 2005/0129564 A1 | 6/2005 | Nakamura et al. | |
| 2005/0246041 A1 | 11/2005 | Kreifeldt et al. | |
| 2005/0266041 A1 | 12/2005 | Gerold et al. | |
| 2006/0052863 A1 | 3/2006 | Harder et al. | |
| 2006/0052864 A1 * | 3/2006 | Harder et al. | 623/1.38 |
| 2006/0246107 A1 | 11/2006 | Harder et al. | |
| 2010/0262221 A1 * | 10/2010 | Schafer et al. | 623/1.13 |

FOREIGN PATENT DOCUMENTS

| | | |
|---|---|---|
| DE | 10 128 100 A1 | 12/2002 |
| DE | 102 53 634 A1 | 5/2004 |
| EP | 1 419 793 A1 | 5/2004 |
| EP | 1 562 565 A2 | 8/2005 |
| EP | 1 632 255 A2 | 3/2006 |
| JP | 9-241778 A | 9/1997 |
| JP | 2000-282165 A | 10/2000 |
| WO | WO 2004/043474 A | 5/2004 |

OTHER PUBLICATIONS

International Search Report of Application No. PCT/EP2008/003585 dated Aug. 17, 2009.
Written Opinion of the International Searching Authority of Application No. PCT/EP2008/003585 dated Aug. 17, 2009.
European Search Report of Application EP 07 01 0557 dated Jan. 10, 2008.
Qiuming Peng et al., "Microstructures and Tensile Properties of Mg-8Gd-0.6Zr-xNd-yY (x+y=3, Mass %) Alloys", Materials Science & Engineering A 433, 2006, pp. 133-138.
Qiuming Peng et al., "Microstructures and Tensile Properties of Mg-8Gd-0.6Zr-xNd-yY (x+y=, Mass%) Alloys", Materials Science & Engineering A: Structural Materials: Properties, Microstructure & Processing, Lausanne, CH, vol. 433, No. 1-2, Oct. 15, 2006, pp. 133-138, XP-005623386.

* cited by examiner

*Primary Examiner* — Kathleen Sonnett
*Assistant Examiner* — Sarah Webb
(74) *Attorney, Agent, or Firm* — Buchanan Ingersoll & Rooney PC

(57) ABSTRACT

The present invention relates to compositions and structure of deformable alloys on the basis of magnesium with an optimum combination of mechanical properties (strength, plasticity) and a resistance to corrosion, including in vivo. Alloys of the new group possess an excellent formability at room temperature, high corrosion stability in sodium chloride solution, excellent heat resistance and can be used in various technical applications, particularly in vivo as a structural material for stents.

19 Claims, No Drawings

MAGNESIUM-BASED ALLOY

FIELD OF THE INVENTION

The present invention relates to compositions and structure of deformable alloys based on magnesium having optimal mechanical properties such as strength, plasticity, etc. or resistance to corrosion, including in vivo. Alloys of the new group have excellent formability at room temperature, high corrosion stability in sodium chloride solution and in a living body, as well as excellent heat resistance. They can be used in various technical fields.

BACKGROUND OF THE INVENTION

Magnesium, a light metal, is an attractive material used in constructions, for example, in the automobile and space industries, for manufacturing of cases for notebooks, mobile phones, etc. However, it has rather a low level of strength, toughness and plasticity, caused by the h.c.p. crystal structure. In addition, magnesium has a low resistance to corrosion because of its strong chemical activity. Thus, the only way to use magnesium in some industrial fields is to create magnesium-based alloys with improved properties.

The influence of alloying elements on mechanical and corrosion properties of magnesium alloys is well studied in binary systems, but in multi component alloys their mutual (namely: combined, joint, aggregate, etc.) influence can appear complex and unpredictable. Therefore, the choice of the basic alloying elements and their interrelation in an alloy has defining influence on its properties.

Industrial alloys of magnesium are subdivided into groups according to additional alloying elements such as lithium, aluminium, zinc, yttrium, etc. For example, under the ASTM specification there are groups of magnesium alloys based on lithium—LA (Mg—Li—Al), LAE (Mg—Li—Al—P3M), aluminium—AM (Mg—Al—Mn), AZ (Mg—Al—Zn), AE (Mg—Al-RE), where RE stands for rare earth metals, based on zinc—ZK (Mg—Zn—Zr), ZE (Mg—Zn-RE) and ZH (Mg—Zn—Th); or on the basis of yttrium—WE (Mg—Y—Nd—Zr), etc.

Many patents describe alloys that have more complex compositions and which cannot be clearly assigned to any class under the ASTM specification. The basic aim for the development of these alloys is improvement of certain properties of magnesium that can be used in various technical fields. Mechanical properties of magnesium alloys as well as other metallic alloys with fixed composition are operated by changing the worked combination of hardening and plastic deformation mechanisms. The latter can be modified, in turn, as due to change of a structural condition of an alloy and so also due to a use of special heat treatments.

Corrosion rate of magnesium strongly depends on its purity. For example, in a 4% water solution of sodium chloride a corrosion rate of magnesium purity of 99.9% is hundreds of times higher than for magnesium with purity of 99.99%.

Alloying elements of an alloy, their distribution as well as the composition of the chemical compounds that they form also influences the resistance to corrosion. The corrosion rate of magnesium alloys depends on the structural condition of an alloy and the methods of manufacturing it. In addition, some impurities can change the requirements for a tolerance range of other alloying elements. So, some introduction of aluminium into a magnesium based alloy can increase an influence of other alloying elements on the corrosion rate of an alloy.

Alloys of the present invention are intended to be used mainly at room temperature and for applications demanding good formability and high corrosion stability. Therefore previous developments regarding improvement of mechanical and corrosion properties of magnesium alloys will be considered below under the specified temperature conditions. The data on improvement of strength-, creep resistance- and corrosion characteristics of magnesium alloys at elevated and high temperatures will be considered only partially. This data will be dropped, because, though the improved strength of such alloys will be maintained at room temperatures, the plastic characteristics in these conditions can be strongly reduced.

Unless specified otherwise, the description of the properties of the known magnesium alloys will relate to the range of temperatures varying from 20-50° C., and the composition of the alloys will always be defined as a percentage on weight. (Note: The definition "percentage on weight" is used most often, but "mass percentage" is truer from the physical point of view, because a body weight is different at different geographical breadths of the Globe, and body mass is constant. Our compositions, we show result below is in "mass percentage".

Mg—Li alloys are the most plastic alloys of magnesium, but their main problem is low corrosion stability and strength. For example, at a room temperature the ultimate elongation of alloy Mg-11% Li reaches 39% at the strength of 104 MPa (see U.S. Pat. No. 2005/6 838 049). However, the corrosion rate of Mg—Li alloys is rather high even in the pure water.

Mg—Li alloys are additionally doped to increase their strength and corrosion stability. Most often aluminium and zinc are added to the alloy to increase strength and corrosion stability. The addition of aluminium and zinc (4% and 2% respectively) leads to a satisfactory combination of strength and deformability of Mg—Li—Al—Zn alloys. It is shown that the addition of 0.6% Al into the alloy Mg-9% Li leads to substantial increase in strength at temperatures below 200° C. in a wide range of deformation rates. Corrosion stability of alloys with such composition increases also.

Some other combinations of alloying elements are available for alloys Mg—Li system. U.S. Pat. No. 2005/6 838 049 describes "Room-temperature-formable magnesium alloy with an excellent corrosion resistance". Its composition includes from 8.0 to 11.0% lithium, from 0.1 to 4.0% zinc, from 0.1 to 4.5% barium, from 0.1 to 0.5% Al, and from 0.1 to 2.5% Ln (the total sum of one or more lanthanides) and from 0.1 to 1.2% Ca, the balance being Mg and inevitable impurities (the balance was not made with magnesium, it was taken as base (or consisted of Mg and inevitable impurities) and alloying elements were added to it). The invention puts emphasis on precipitation of the phase $Mg_{17}Ba_2$ ($Mg_{17}Ba_2$ is a chemical combination named in crystallography as "phase"), providing refinement and uniform dispersion of an alpha- and beta-phases of alloy matrix. Such structure raises the strength of an alloy. However, though barium has b.c.c. lattice, it has a low solubility limit in Mg and forms intermetallic compounds $Mg_{17}Ba_2$ that noticeably reduce plastic characteristics of Mg—Li alloys.

U.S. Pat. No. 1991/5 059 390 describes "a dual-phase magnesium-based alloy consisting essentially of about 7-12% lithium, about 2-6% aluminum, about 0.1-2% rare earth metal, preferably scandium, up to about 2% zinc and up to about 1% manganese. The alloy exhibits improved combinations of strength, formability and/or corrosion resistance".

JP Pat. No. 1997/9 241 778 discloses a magnesium alloy being used as a construction material, containing up to 40%

Li and one more additive from the following: up to 10% Al, up to 4% Zn, up to 4% Y, up to 4% Ag and up to 4% RE.

In U.S. Pat. No. 1993/5 238 646 the method of preparation of an alloy having an improved combination of strength, formability and corrosion resistance is described. The specified alloy includes 7-12% lithium, 2-7% aluminium, 0.4-2% rare earth metal, up to 2% zinc and up to 1% manganese, the balance being magnesium and impurities. Purity of the magnesium taken for a basis of an alloy is 99.99%.

Mg—Al alloys are most widespread class of magnesium alloys for various applications (groups: AM, AZ, AE etc.). However, though they show raised corrosion resistance and have higher strength, they are much less plastic than Mg—Li alloys. Various combinations of alloying elements are offered for improvement of the certain properties of this class of alloys.

U.S. Pat. No. 2005/0 129 564 describes an alloy consisting of 10 to 15% Al, 0.5 to 10% Sn, 0.1 to 3% Y and 0.1 to 1% Mn, the balance being Mg and inevitable impurities. The magnesium alloy exhibits good creep properties and is particularly suitable for engine related parts.

U.S. Pat. No. 2002/6 395 224 describes an alloy which "includes magnesium as a main component, boron of 0.005 weight % or more, manganese of 0.03 to 1 weight %, and substantially no zirconium or titanium. This magnesium alloy may further include aluminum of 1 to 30 weight % Al and/or zinc of 0.1 to 20 weight %. Because of appropriate amounts of boron and manganese contained in the magnesium alloy, the grain of the magnesium alloy is refined." The structure refinement leads to increased mechanical characteristics of this alloy.

In U.S. Pat. No. 2005/0 095 166 is disclosed a heat resistant magnesium alloy for casting that includes 6-12% aluminum, 0.05-4% calcium, 0.5-4% rare earth elements, 0.05-0.50% manganese, 0.1-14% tin, balance are magnesium and inevitable impurities. The problem of this invention is the improvement of heat resistance for the magnesium alloy.

Among Mg—Zn alloys the mostly known alloys are: ZK (magnesium-zinc-zirconium) having good strength and plasticity at a room temperature, ZE (magnesium-zinc-RE) having average strength and ZH (magnesium-zinc-thorium) having high room-temperature yield strength in the aged condition (T5). However, alloys containing thorium are not manufactured anymore because of their radioactive components.

U.S. Pat. No. 2001/6 193 817 describes another magnesium based alloy for high pressure die casting (HPDC), providing good creep and corrosion resistance. The alloy comprises at least 91 weight percent magnesium, 0.1 to 2 weight percent of zinc, 2.1 to 5 percent of a rare earth metal component and 0 to 1 weight percent calcium.

However, Al and Zn and some other alloying elements improve strength and corrosion characteristics of Mg alloys and simultaneously reduce their plasticity. In addition, these elements are unsuitable for using alloys in structural elements of endoprosthesises (not biocompatible).

Among Mg-RE alloys compositions of the WE type (Mg—Y—Nd—Zr) are the most known. These alloys have quite a good formability and increased corrosion resistance. According to the specification of the Manufacturer (Magnesium Elektron Ltd., Manchester, England) the ultimate elongation for alloy ELEKTRON WE43 can reach 16% at a room temperature, and the corrosion rate is equal 0.1-0.2 mg/cm$^2$/day (B117 salt spray test) or 0.1 mg/cm$^2$/day (sea water immersion test). However, in many cases deformability of alloy WE43 is insufficient, and the spread of mechanical characteristics for ingots is very great: the elongation varies from 2-17%, in average 7%, data of the Manufacturer for 215 samples. When deformed and treated for stabilization and age-hardening (condition T6), alloys WE43 show more stable, but still low plasticity at a room temperature—up to 10%.

Various changes of a composition of Mg-RE alloys are offered how to increase their characteristics. U.S. Pat. No. 2003/0 129 074 describes high temperature resistant magnesium alloys containing at least 92% magnesium, 2.7 to 3.3% neodymium, 0.0 to 2.6% yttrium, 0.2 to 0.8% zirconium, 0.2 to 0.8% zinc, 0.03 to 0.25% calcium and 0.00 to 0.001% beryllium. The alloy may additionally contain up to 0.007% iron, up to 0.002% nickel, up to 0.003% copper and up to 0.01% silicon and incidental impurities.

Corrosion stability of any magnesium alloys lowers inversely with the Fe, Ni and Cu impurity levels. According to the prior art, alloy AZ91E has a corrosion rate in salt fog tests 100 times lower than alloy AZ91C, due to the higher purity of its alloy basis (0.015% Cu, 0.001% Ni, 0.005% Fe, the others of 0.3% max—in the alloy AZ91E, and 0.1% Cu, 0.01% Ni, the others of 0.3% max—in the alloy AZ91C).

The JP Pat. No. 2000/282 165 describes an Mg—Li alloy with the improved corrosion resistance. The alloy contains up to 10.5% Li and magnesium with a concentration of iron<=50 p.p.m., which is provided by a fusion in a crucible that is covered by chrome and its oxide.

During the last decade interest appeared on the magnesium alloys as material suitable for construction of vascular (coronary and peripheral) endoprosthesises (stents).

Stents are implanted into a vessel lumen after carrying out a percutaneous transluminal coronary angioplasty (PTCA), while the narrowed (stenosis) vessel lumen is expanded by means of an inflated balloon, after the balloon has been positioned at the affected site of the vessel. Stents in form of scaffolds prevent the collapse of the expanded vessel and provide the necessary blood stream through the lumen.

One of the side effects of angioplasty is the phenomenon called restenosis, a rapid proliferation of smooth muscle cells inside the vessel lumen caused by the injury of PTCA. The smooth muscle cells proliferation lasts generally 1-3 weeks. This effect is currently prevented by the use of stents coated with drugs, such as sirolimus or paclitaxel. Unfortunately, because cell proliferation is sometimes prevented too efficiently, the metallic surface of the stent may remain uncoated for months and may provoke the occurrence of coronary thrombosis, sometimes months or years after the coated stent has been implanted in the artery. This may lead to sudden death, sometimes many years after the stent implantation.

As aforesaid, many researchers are interested in biosoluble, biodegradable, or bioresorbable stents. The important advantage of such stents consists in a slow dissolution in vivo of the stent structural material and in gradual disappearance of this device after it has executed its medical function of supporting the vessel wall. In such a way, the disappearance of the stent will avoid the occurrence of thrombosis formation.

Stent materials should have particular mechanical characteristics in order to withstand the elastic recoil due to the vessel wall pressure (radial stability) and to increase the initial stent diameter (for example, under an action of balloon pressure) up to the working size without destruction of stent struts. Besides, the material of stents should be biocompatible, free of harmful impurities, and should not elute toxic substances during degradation in vivo (see U.S. Pat. No. 2005/0 246 041).

Some of the known biosoluble stents are made from various organic polymers having very low mechanical characteristics. These stents are bulky and temperature-sensitive.

Most perspective materials for the manufacturing of biodegradable stents are metallic alloys which may be dissolved in liquids and tissue of a living body (in vivo). Magnesium alloys have been explored for this purpose.

DE Patent No. 2002/10 128 100 describes a medical implant made from magnesium alloy containing additions of rare earth metals and lithium with the following preferred features: 0-7 wt. % lithium, 0-16 wt. % aluminum and 0-8 wt. % rare earth metals. The rare earth metals are cerium, neodymium and/or praseodymium. Examples of alloys are Mg Li4 Al4 SE2 (where SE=rare earth) or MgY4SE3Li2.4. This patent describes experiments on animals too, with stents made from the AE21 alloy and which efficiency is evaluated.

US Pat. No. 2004/0 241 036 discloses further medical implant for the human or animal body made from an alloy that consists at least partially of a magnesium alloy. The magnesium alloy contains portions of rare earth metals and lithium and optionally yttrium and aluminum. The magnesium alloy preferably contains lithium in a portion of 0.01 to 7 mass %, aluminum in a portion of 0.01 to 16 mass %, optionally yttrium in a portion of 0.01 to 7 mass % and rare earth metals in a portion of 0.01 to 8 mass %.

US Pat. No. 2004/0 098 108 describes endoprostheses with a carrier structure, which contains a metallic material, wherein the metallic material contains a magnesium alloy of the following composition: magnesium>90%, yttrium 3.7%-5.5%, rare earths 1.5%-4.4% and balance<1%. This composition corresponds essentially to the alloy WE43.

Other patents of the same inventors (EP 2004 1 419 793, WO 2004 043 474, EP 2005/1 562 565, US 2005/0 266 041, US 2006/0 052 864, EP 2006/1 632 255, US 2006/0 246 107) are variants of the initial document, the DE Pat. No. 10 (2) 53 634.1, priority date Nov. 13, 2002. They carry different names ("Endoprosthesis", "Endoprosthesis with a supporting structure of magnesium alloy", "Use of one or more elements from the group containing yttrium, neodymium and zirconium", "Implant for vessel ligature" etc.) and various items in the claims (time of dissolution in vivo, medical efficiency of alloy components), but all have one common subject, i.e. stents made of the type WE43 alloy.

The search for a suitable material is complicated and expensive (US Pat. No. 2005/0 266 041). All previously known solutions have hitherto not led to a satisfactory result. Apparently, from this point of view, the aforementioned group has been chosen for stent manufacturing the industrial alloy WE43 provides a good (for magnesium alloys) combination of corrosion stability and plasticity.

However, the WE43 alloy is apparently not optimal as a constructional material for manufacturing of biosoluble stents (insufficient plasticity and corrosion stability in vivo). As a proof of this impression one may have a look at the last patents of the specified inventors—the US Pat. No 2006/0 052 863. A wide variation of concentration of the basic alloying elements is patented in it: Y: 2-20%, RE: 2-30%, Zr: 0.5-5.0%, balance: 0-10%, Mg—up to 100%. It is particular to emphasize that the alloying set still coincides with a set of the WE43 alloy.

The document "Peng et al: "Microstructures and tensile properties of Mg-8Gd-0.6Zr-xNd-yY (x+y=3, mass %) alloys" Materials Science And Engineering A: structural Materials: Properties, Microstructure & Processing, Lausanne, CH, vol. 433, no. 1-2, 15 Oct. 2006 (2006-10-15), pages 133-138, XP005623386 ISSN: 0921-5093" discloses the alloy Mg-8Gd-0.6Zr-2Nd-1Y (page 133, column 2, alloy (B); Nd being a rare earth metal) having a fine grain size of 60-120 um (p. 134, col. 2, end).

The mechanical characteristics and corrosions rates of some most widely known magnesium-based alloys are summarized in the table 1 (data are taken from different sources).

TABLE 1

Comparative characteristics of some magnesium alloys

| ALLOY | YS, MPa | UTS, MPa | Ultimate elongation, % | Corrosion rate (condition unknown) | Condition |
|---|---|---|---|---|---|
| WE43* | 195 | 280 | 10 | 0.1 mg/cm$^2$/day (sea water immersion) 0.1-0.2 mg/cm$^2$/day ASTM B 117 salt spray test | Extruded, T5 |
| WE43 | 180 | 300 | 10 | — | Forging, T5 |
| WE43 | 190 | 270 | 16 | 2.5 mg/cm$^2$/day** | Extruded, T4 |
| AZ 91D | 160 | 230 | 3 | <0.13 mg/cm$^2$/day ASTM B 117 salt spray test | Cast, F |
| AM 60B | 130 | 220 | 6-8 | <0.13 mg/cm$^2$/day ASTM B 177 salt spray test | Cast, F |
| AZ 61 | 230 | 310 | 16 | | Deformed, F |
| ZK 60 | 295 | 360 | 12 | | Deformed, T5 |
| AM 160 | 130 | 220 | 8 | | Cast, F |
| Mg—11Li | — | 105 | 39 | | Cast, F |
| Alloy of invention, example 1 | 215 | 290 | 25 | 1.1** | Deformed, H2 |
| Alloy of invention, example 2 | 190 | 275 | 29 | 1.8** | Deformed, H2 |

*Letters in names of alloys designate: A—aluminium, E—the rare earth metals (RE), K—zirconium, L—lithium, M—manganese, W—yttrium, Z—zinc; and figures - the maintenance of an alloying element approximated to an integer in percentage.
**The tests for corrosion were led by a special technique. Corrosion rate was calculated after staying of specimens in a stream of 0.9% sodium chloride solution at a flow rate of 50 m/minute. Corrosion rate was defined on the loss of specimen weight and by quantity of the magnesium, which excreted into the solution. Data of measurements were averaged. Such test scheme allows continuously deleting the product of corrosion from sample surface, which deform results of the corrosion rate measurement by method of sample weight loss measurement.

THE SUMMARY OF THE INVENTION

It is an object of the invention to provide a new kind of magnesium alloy for a wide field of applications. The alloy should have an improved combination of strength, plasticity and corrosion resistance, high formability at the room temperature. The latter gives an opportunity of obtaining a certain form by usual methods of metals processing—extrusion, forging, rolling, drawing etc.

In the first preferred embodiment the invention provides a magnesium based alloy comprising:

Indium in an amount between 0.1 and 4.0 mass %,
Scandium in an amount between 0.1 and 15.0 mass %,
Yttrium in an amount between 0.1 and 3.0 mass %,
Rare earth metals in an amount between 0.1 and 3.0 mass %,
Zirconium in an amount between 0.1 and 0.7 mass %,
Other impurity (including unavoidable impurities) up to 1 mass % (in the sum) and the balance being made up to 100% with magnesium having purity of 99.98 mass % (only metal impurity are considered) or higher. (We do not consider nonmetallic impurities such as oxygen, hydrogen nitrogen etc.)

Impurities, including unavoidable impurities, may be present in an amount of 1 mass % or less.

According to another advantageous embodiment, gallium may be used instead of indium in an amount of 0.1-4.0 mass %. Alternatively, gallium may be used together with indium in a combined amount of 0.1-4.0 mass %.

According to another advantageous embodiment, gadolinium may be used instead of scandium, in an amount of 0.1-15.0 mass %. Alternatively, gadolinium may be used together with scandium in a combined amount of 0.1-15.0 mass %.

According to another advantageous embodiment, hafnium and/or titanium may are used instead of zirconium, in an amount of 0.1-0.7 mass %. Alternatively, hafnium and/or titanium may be used together with zirconium in a combined amount of 0.1-0.7 mass %.

According to advantageous embodiments, the content of iron, nickel and copper in the present alloy should not exceed 0.002 mass % when the alloy is a high corrosion resistance alloy.

According to advantageous embodiments, the present magnesium alloy has an ultra fine-grained structure with the grain size less than of 3 microns.

According to advantageous embodiments that concern medical applications, the alloy of the invention does not contain elements that are toxiferous and harmful to a living organism such as, but not limited to, argentum (Ag), aluminium (Al), beryllium (Be), cadmium (Cd), chromium (Cr), mercury (Hg), strontium (Sr) and thorium (Th) in concentrations equal to or more than 0.001 mass % per element. All relevant embodiments are already listed above.

THE DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings. The recitation of numerical ranges by endpoints includes all integer numbers and, where appropriate, fractions subsumed within that range (e.g. 1 to 5 can include 1, 2, 3, 4 when referring to, for example, a number of items, and can also include 1.5, 2, 2.75 and 3.80, when referring to, for example, masses). The recitation of end points also includes the end point values themselves (e.g. from 1.0 to 5.0 includes both 1.0 and 5.0). Unless otherwise stated, all percentages, when expressing a quantity, are weight percentages.

Table 1 shows that various magnesium alloys have essentially differing sets of mechanical and corrosion characteristics. Some of them have higher strength, while others are less strong but are more deformable. However, it is desirable for some applications to combine high strength with high plasticity, high deformability and corrosion stability at room temperatures.

It is an aim of the present invention to provide a new kind of magnesium alloy for a wide field of applications. The alloy should have an improved combination of strength, plasticity and corrosion resistance, and high formability in comparison with existing alloys. The high formability allows certain forms to be made by usual methods of metals processing—extrusion, forging, rolling, drawing etc.

It is desirable, for example, to develop an alloy having yield stress at room temperature of more than 210 MPa, ultimate tensile strength of more than 300 MPa, elongation up to rupture of more than 25% and corrosion resistance in water and sodium chloride solutions better than for the alloy WE 43.

As mentioned above the invention provides a magnesium based alloy comprising or consisting of:
Indium in an amount between 0.1 and 4.0 mass %,
Scandium in an amount between 0.1 and 15.0 mass %,
Yttrium in an amount between 0.1 and 3.0 mass %,
Rare earth metals in an amount between 0.1 and 3.0 mass %,
Zirconium in an amount between 0.1 and 0.7 mass %,
Other impurity (including unavoidable impurities) up to 1 mass % (in the sum) and the balance being made up to 100% with magnesium having purity of 99.98 mass % (only metal impurity are considered) or higher.

According to one aspect of the invention, the magnesium is ultrapure with a total impurities content of 0.02, 0.015, 0.01, 0.05, 0.03, preferably 0.02 mass % or less. Content of Fe, Ni and Cu, having the most adverse influence on corrosion characteristics of magnesium is generally present in the magnesium in an amount of 0.002 mass % of each element, or less.

According to another aspect of the invention, the alloy contains alloying elements in the quantities that do not exceed considerably their solubility in magnesium. According to another aspect of the invention, the purity of each alloying element is 99.98 mass % or higher, i.e. each has 0.02 mass % or less metal impurities.

Elements that work most favorably upon the certain alloy characteristics and not changing essentially other characteristics have been chosen as the basic alloying elements.

For medical applications, the new alloy should not contain elements harmful and toxic for living organism in appreciable quantities, for example, above the biological maximum concentration limits. It is simultaneously desirable to have in an alloy composition such elements that could have a positive influence upon a living body.

For additional (besides alloying) improvement in the combination of mechanical and corrosion characteristics of offered alloys, the alloy should be used in ultra fine-grained condition with grain size of 4, 3, 2, 1, microns or less, preferably 3 microns or less. The specified grain structure is created in preliminary forged ingot by methods of programmed intensive plastic deformation in combination with programmed heat treatment. The methods of processing should be applied at intensive plastic deformation of preforms that provide the needed prevalence of shear stress in materials that are processed.

The invention, by consideration of alloying elements, discriminates the group RE metals (elements with numbers from 57 up to 71 in the Periodic table) and both yttrium and scandium that, though they have an identical structure of external electronic shells with RE metals and similarity of some chemical properties, but should be differed from them in alloys compositions, according to ASTM standard (due to their differing influence on alloys).

On the basis of the above mentioned preconditions, available references and own research the invention offers the following alloying elements for the new kind of alloys manufactured on the basis of magnesium.

Indium

Our research on the multi-component magnesium alloys has revealed that the addition of indium in alloys of the Mg—Sc—Y-RE-Zr system leads to abrupt grain refinement during crystallization thereof.

Further it has been established that due to an initial fine-grained structure of an ingot, such alloys containing indium are perfectly deformed during the subsequent thermal-mechanical processing with the purpose of further grains refinement. Moreover, the received semifinished products (after extrusion, blacksmithing or equal-channel angular extrusion) possess the unique for magnesium alloys formability: at room temperature the alloy withstand (without fracture) deformations up to 90% by drawing (some passes) and up to 30% by rolling (per one pass) without intermediate annealings. Such a high deformability is only possible for some binary alloys Mg—Li.

Besides, it was unexpectedly found out that alloys of the Mg—In—Sc—Y-RE-Zr system possess unique heat resistance. The grain structure of such alloys does not change even after many hours withstanding at the temperatures of 450-470° C. This allows to carry out hot deformation of such alloys without losing the before reached mechanical properties.

Mechanical tests of such alloys at room temperature have also shown very high results. Depending on a concrete composition and thermal-mechanical treatment following results (for single property) have been attained: yield stress up to 300 MPa, ultimate tensile stress up to 400 MPa and elongation up to 29%.

Corrosion test (the method was described in remarks to Table 1) has shown that addition of indium into an alloy of the system Mg—Sc—Y-RE-Zr leads to reduction of the corrosion rate twice in comparison with the corrosion rate of the WE43 alloy.

As far as medical applications are concerned, the present alloys can be used safely, for example in implants such as stents and plates. Data regarding toxicity and common influence of, for example, indium chemical compounds on humans indicate it is safe; it is included in the FDA's GRAS list (Generally Recognized as Safe) even though indium is sometimes classified as a heavy metal with no officially recognized nutritional or physiological function. U.S. Pat. No. 4,591,506 shows that indium and its compounds are applied in a vitamin or mineral composition for a variety of uses including increasing the detoxification rate of the liver. And the further U.S. Pat. No. 4,182,754 shows that indium may be used to normalize the activity of the thyroid gland.

In one other preferred embodiment, indium can be replaced in the same quantities with gallium that offers similar influence on properties in the offered alloy. Simultaneously, alloying of magnesium with indium and gallium is also possible.

The amount of indium and/or gallium present in the magnesium based alloy may be 0.1, 0.5, 1, 1.5, 2, 2.5, 3, 3.5 or 4.0 mass %, or a value in the range between any two of the aforementioned values. Preferably it is between 0.1 and 4.0 mass %.

Scandium

According to various data, scandium has a limit of solubility in magnesium up to 28%. Laboratory findings have shown that addition of scandium to magnesium within the limits up to 15% provides creation of Mg—Sc solid solution. It increases plasticity and strength of the alloy and slightly increases corrosion rate in the sodium chloride solution (at scandium content more than 5%). For scandium with higher concentration (up to 15%) the corrosion rate of Mg—Sc alloys can increase many times.

Scandium is also good modifier of grain structure of magnesium ingots. According to Russian Patents No. 283 589 and No. 569 638, scandium additions to magnesium-based alloys improve foundry characteristics, corrosion resistance and/or mechanical strengths.

Precipitation of Mg—Sc phase is possible during high-temperature processing of magnesium alloys with the big contents of scandium. Very thin intermetallic bond in the form of plates precipitates during the solution and forms in the direction <1120> in the basal plane. The plates distribute non-uniformly and do not make any hardening at the room temperature when the main mechanism of deformation is basal sliding.

The properties of scandium are also exhibited by gadolinium; consequently scandium may be replaced by gadolinium, or the alloy may comprise a mixture of scandium and gadolinium.

The amount of scandium and/or gadolinium present in the magnesium based alloy may be 0.1, 0.5, 1, 1.5, 2, 2.5, 3, 3.5, 4, 5, 6, 7, 8, 9, 10, 11, 12, 13, 14 or 15.0 mass %, or a value in the range between any two of the aforementioned values. Preferably it is between 0.1 and 15.0 mass %.

Yttrium

Yttrium has the limit of solubility in magnesium about 2-6% (according to various references) at room temperature. The addition up to 3% of yttrium to magnesium increases its strength without essential reduction in plasticity and in corrosion resistance of Mg—Y alloy. Yttrium could also influence the suppression of smooth muscles cell proliferation (restenosis prevention), etc.

The amount of yttrium present in the magnesium based alloy may be 0.1, 0.5, 1, 1.5, 2, 2.5, 3.0 mass %, or a value in the range between any two of the aforementioned values. Preferably it is between 0.1 and 3.0 mass %.

Rare Earth Metals (RE)

The influence of rare earth metals on properties of magnesium alloys depends on their solubility in magnesium alloys and their melting point. Solubility of RE in solid magnesium ranges from practically zero (La) up to 7 percent (Lu). Metals from group with nuclear numbers from 64 (Gd) up to 71 (Lu) have melting temperatures and limits of solubility in magnesium higher than metals of cerium group. Alloying up to 3% RE with magnesium raises creep and corrosion resistance of them. Besides, rare earth metals reduce micro-porosity of magnesium alloys during production of an initial ingot.

The amount of rare earth metals present in the magnesium based alloy may be 0.1, 0.5, 1, 1.5, 2, 2.5, 3.0 mass %, or a value in the range between any two of the aforementioned values. Preferably it is between 0.1 and 3.0 mass %.

Zirconium Zirconium is a known basic element that makes grain refinement in magnesium alloys during ingot smelting. The fine-grained ingot is easier exposed to preliminary and subsequent deformations.

As one of primary embodiments, zirconium can be replaced with hafnium or titanium that exerts similar influences on properties of an alloy.

The total amount of zirconium and/or hafnium and/or titanium present in the magnesium based alloy may be 0.1, 0.2, 0.3, 0.4, 0.5, 0.6 or 0.7 mass %, or a value in the range between any two of the aforementioned values. Preferably it is between 0.1 and 0.7 mass %.

It is known that metallic materials with the ultra fine-grained (UFG) structure show higher level of mechanical characteristics and have higher deformability. Usual (industrial) methods of deformation processing of metals allow a grain size not less than 15-30 micrometers to be achieved; this is not sufficient for some essential increase of their strength and plastic characteristics.

The necessary increasing of materials' properties can be provided only due to UFG structures with grain size of 0.1-3.0 microns. However, it is difficult to create such structures in materials having low plasticity in initial conditions (for example, in ingots).

Authors have found the UFG structure with the grain size of 0.3-1.0 microns can be achieved by a method of repeated alternation of extrusion and settlement in a complex with the programmed heat treatment for such non-conventional materials as beryllium and niobium-titanium superconducting alloys. Their strength is increased by 30% and plasticity many times. Then, the developed methods have been applied to intensive deformation of magnesium and to other low-ductility alloys. Furthermore, it has been found that the use of pressure with a high component of shear stress (repeated alternation of an extrusion and settlement) in combination with programmed heat treatment also leads to the effect of essential grain refinement. It is also possible to use an intensive deformation with changing of materials' flow direction for the creation of shear stress during the processing of materials.

Named methods allow achieving (after subsequent heat treatment) some grain size and sub-grain size up to 0.1 micrometers and less. Such grain structure supply high plasticity and strength simultaneously. This will provide high operational properties of material in any design and for any purpose.

Further setting up of any necessary product form (for practical using) can be made according to any known technological schemes: rolling, extrusion, press forming etc.

Inventors, on the basis of the existing references and their own research, have chosen as preferable embodiments the following declared compositions of magnesium alloy that have the best combination of mechanical and corrosion characteristics at the room temperature and also high heat resistance (among the known magnesium-based alloys).

Any combination of the basic alloying elements in a following range of amounts (in mass %): indium (or gallium or both) from 0.1% to 4.0%, yttrium from 0.1% to 3.0%, scandium (or gadolinium or both) from 0.1% to 15.0%, RE from 0.1% to 3.0%, zirconium (or hafnium or titanium or any of their combinations) from 0.1% to 0.7%, other (including inevitable) impurities up to 1.0%, whereby the basis of an alloy is magnesium with purity of 99.98% added up to 100%.

Contents of iron, nickel and copper in alloys should not exceed 0.002 mass % per element.

The inventive alloys that are provided for medical applications should not contain any toxic elements (including Ag, Al, Be, Cd, Sr, Th etc.) in appreciable quantities that could influence the living body.

The magnesium-based multi-component alloys of the present invention with a grain size no more than 3 microns provide fine formability (including room temperature), excellent corrosion resistance in sodium chloride solution and high heat resistance.

The alloys of the present invention are prepared using standard methods for the preparation of magnesium-based alloys as described, for example in [Lipnitsky A. M., Morozov I. V. Technology of nonferrous castings. -L: Mashgiz, 1986. -224 pp].

Generally, the alloy of the invention is prepared by the direct fusion of magnesium with the specified elements in a high-frequency induction furnace having an atmosphere of high purity argon and in a high purity graphite crucible. For full dissolution of all components, the alloy is stood in the crucible at the temperature of 700, 710, 720, 730, 740, 750, 760, 770, 780, 790, 800, 810, 820, or 830 deg C. or a temperature in a range between any two of the aforementioned values, preferably between 760 to 780 deg C. The crucible is allowed to stand for 5, 10, 15, 20, 25, 30, 35, 40, 45, 50, 55 or 60 minutes, or for a period in a range between any two of the aforementioned values, preferably between 10 and 20 minutes. The alloy is poured out into a cooled steel mold with a special daubing by method of bottom teem. The ingot obtained may be extruded at temperature of 300, 310, 320, 330, 340, 350, 360, 370, 380, 390 or 400 deg C., or a temperature in a range between any two of the aforementioned values, preferably between 330 to 370 deg C. The obtained semi-finished product may be subjected to deformation by equal-channel angular extrusion. This may be performed at a temperature of 270, 280, 390, 300, 310, 320, 330 or 340, or a temperature in a range between any two of the aforementioned values, preferably between 300 to 340 deg C., for a number of extrusion cycles. The number of extrusion cycles will depend on the composition of the alloy but generally, will be 8, 9, 10, 11, 12, cycles, or a number in a range between any two of the aforementioned values, preferably between 6 and 8 extrusion cycles. There may be intermediate annealing at a temperature of 400 to 460 deg C., preferably at 430 deg C. for 2-3 cycles (to achievement of micro-hardness $H_\mu$ of 100 kg/mm$^2$).

The inventive alloys have been prepared by using standard (conventional) methods of Mg alloys melting.

The alloy of the present invention can be used in medical devices which have contact the body. It may be used, for example, as part of a screw, bolt, plate, staple, tubular mesh, stent, spiral, coil, marker and catheter.

EXAMPLES

Example 1

Alloy consists essentially of magnesium with purity of 99.997% with addition of (mass %) 2.0% indium, 5.2% scandium, 2.4% yttrium, 3.0% the rare earth and 0.4% zirconium. Contents Fe, Ni and Cu do not exceed 0.002% of each, and contents of incidental elements and impurities do not exceed 0.05%.

The alloy was made during the direct fusion of magnesium with the preliminary prepared master alloy with the specified elements in a high-frequency induction furnace having an atmosphere of high purity argon and in a high purity graphite crucible.

For full dissolution of all components, the alloy was stood in the crucible at the temperature of 770° C. within 15 minutes and then was poured out into a cooled steel mold with a special daubing by method of bottom teem.

The obtained ingot (diameter of 50 mm) was extruded at the temperature of 350° C. with the extrusion ratio of 3:1.

The obtained semi-finished product has been subjected to deformation by equal-channel angular extrusion at the temperature of 320° C., number of cycles of extrusion 12, with intermediate annealing at the temperature of 430° C. through 2-3 cycles (at achievement of micro-hardness $H_\mu$ of 100 kg/mm$^2$).

Samples have been cut out from the obtained extrudate for the tensile test at room temperature and tests for corrosion behaviour (in a stream of 0.9% sodium chloride solution and speed of the stream of 50 m/min).

Test Results

Mechanical properties (after annealing at the temperature of 430° C. within one hour): YS=215 MPa, UTS=290 MPa, elongation=25%.

Corrosion ratio (obtained by a measurement of the weight loss of specimens and quantitative definition of the magnesium, which has passed in the solution, through the fixed time intervals): 1.1 mg/cm$^2$/day.

Results of the tests show that the alloy according to the invention has the best combination of mechanical and corrosion properties in comparison with the most widespread industrial alloys of magnesium (see Tabl. 1).

Example 2

The ingot on the basis of magnesium with purity of 99.99%, with addition of (mass %): 1.6% indium, 9.0% scandium, 2.7% yttrium, 2.0% rare earth and 0.5% zirconium. Contents Fe, Ni and Cu do not exceed of 0.002% each, and contents of other impurities in the alloy do not exceed 0.01%. The ingot was obtained by the method specified in the example 1.

The ingot was further subjected to deformation by alternation of cycles extrusion (the extrusion ratio 5:1) and upsetting up to initial diameter at the temperature of 340-360° C., (number of cycles 5), with intermediate annealing at the temperature of 400° C. after every cycle.

Samples have been cut out from the obtained preparation for the mechanical tests and tests for corrosion (in a stream of 0.9% water solution of sodium chloride and a speed of the stream of 50 m\min).

Test Results.

Mechanical properties (after annealing at the temperature of 470° C. within one hour): YS=190 MPa, UTS=275 MPa, elongation=29%. Corrosion ratio (in a stream) was 1.8 mg/cm$^2$/day.

Results of the tests show that the alloy according to the invention has the best combination of deformability and corrosion properties and satisfactory strength in comparison with the most widespread industrial alloys of magnesium.

The invention claimed is:
1. A magnesium-based alloy comprising:
Indium, or gallium, or a combination of indium and gallium, in an amount between 0.1 and 4 mass %,
Scandium or gadolinium, or a combination of scandium and gadolinium in an amount between 0.1 and 15.0 mass %,
Yttrium in an amount between 0.1 and 3.0 mass %,
Rare earth metals other than scandium, gadolinium and yttrium in a total amount between 0.1 and 3.0 mass %,
One or more of zirconium, hafnium and titanium in a total amount between 0.1 and 0.7 mass %, and
Magnesium with purity more than or equal to 99.98 mass % making up the balance.

2. The alloy according to claim 1, whereby:
iron impurity is present in an amount of 0.002 mass % or less,
nickel impurity is present in an amount of 0.002 mass % or less, and
copper impurity is present in an amount of 0.002 mass % or less.

3. The alloy according to claim 1, having a structure which is ultra fine-grained and a grain size is less than or equal to 3 microns.

4. The alloy according to claim 1, comprising 0.001 mass % or less of a toxiferous element.

5. The alloy according to claim 1, whereby argentums (Ag), aluminium (Al), beryllium (Be), cadmium (Cd), chromium (Cr), mercury (Hg), strontium (Sr) and thorium (Th) are each present in an amount of 0.001 mass % or less.

6. The alloy as defined in claim 1 in combination with a medical device.

7. A medical device comprising an alloy as defined in claim 2.

8. The alloy of claim 6, wherein said medical device or part thereof is a screw, bolt, plate, staple, tubular mesh, stent, coil, marker and catheter.

9. A medical screw comprising an alloy as defined in claim 1.

10. An endoprosthesis comprising an alloy as defined in claim 1.

11. A medical bolt comprising an alloy as defined in claim 1.

12. A medical plate comprising an alloy as defined in claim 1.

13. A medical staple comprising an alloy as defined in claim 1.

14. A medical tubular mesh comprising an alloy as defined in claim 1.

15. A medical stent comprising an alloy as defined in claim 1.

16. A medical coil comprising an alloy as defined in claim 1.

17. A medical X-ray marker comprising an alloy as defined in claim 1.

18. A medical catheter comprising an alloy as defined in claim 1.

19. The alloy according to claim 3 in combination with a medical product.

* * * * *